(12) United States Patent
Hsu

(10) Patent No.: US 12,383,188 B2
(45) Date of Patent: Aug. 12, 2025

(54) FEEDBACK DEVICE FOR SENSE OF TASTE, AND FEEDBACK SYSTEM AND FEEDBACK METHOD FOR USING THE SAME

(71) Applicant: KINPO ELECTRONICS, INC., New Taipei (TW)

(72) Inventor: Chieh-Li Hsu, New Taipei (TW)

(73) Assignee: KINPO ELECTRONICS, INC., New Taipei (TW)

( * ) Notice: Subject to any disclaimer, the term of this patent is extended or adjusted under 35 U.S.C. 154(b) by 790 days.

(21) Appl. No.: 17/706,559

(22) Filed: Mar. 28, 2022

(65) Prior Publication Data

US 2023/0248298 A1    Aug. 10, 2023

(30) Foreign Application Priority Data

Feb. 9, 2022  (TW) .................................. 111104751

(51) Int. Cl.
*A61B 5/00* (2006.01)
*H04N 21/234* (2011.01)

(52) U.S. Cl.
CPC .......... *A61B 5/4017* (2013.01); *A61B 5/7225* (2013.01); *H04N 21/234* (2013.01)

(58) Field of Classification Search
CPC ... A61B 5/4017; A61B 5/7225; H04N 21/234
See application file for complete search history.

(56) References Cited

U.S. PATENT DOCUMENTS

| 2007/0126927 A1* | 6/2007 | Yun | A63J 5/00 348/473 |
| 2023/0248163 A1* | 8/2023 | Hsu | C12G 3/06 220/574 |
| 2023/0248298 A1* | 8/2023 | Hsu | H04N 21/84 600/300 |

(Continued)

FOREIGN PATENT DOCUMENTS

| CN | 1729934 A | 2/2006 |
| CN | 107704088 A | 2/2018 |
| EP | 0508939 A2 | 10/1992 |

(Continued)

OTHER PUBLICATIONS

Office Action dated May 16, 2023 of the corresponding Japan patent application No. 2022-033739.

(Continued)

*Primary Examiner* — Paul R Durand
*Assistant Examiner* — Michael J. Melaragno
(74) *Attorney, Agent, or Firm* — Chun-Ming Shih; hdls ipr services

(57) ABSTRACT

A feedback device, a feedback system, and a feedback method for taste sense is disclosed, wherein the feedback device includes a processor, a container, and a providing mechanism. Multiple taste materials are stored in the container. When a media player plays a multimedia file to a labeled paragraph, a control signal is sent to the feedback device. After receiving the control signal, the processor controls the providing mechanism to provide a correspond- (Continued)

ing one of the taste materials for the user to eat. Therefore, the user may obtain taste feedback that is relevant to the label paragraph of the multimedia file through the feedback device.

7 Claims, 8 Drawing Sheets

(56) References Cited

U.S. PATENT DOCUMENTS

2024/0186007 A1* 6/2024 Howard ................ A61B 5/076
2025/0031735 A1* 1/2025 Hsu ........................ A23L 27/70

FOREIGN PATENT DOCUMENTS

| EP | 4228272 A1 * | 8/2023 | ........... A61B 5/4017 |
| JP | 2020123070 A | 8/2020 | |
| PT | 97283 A * | 6/1992 | ............. A61L 9/125 |

OTHER PUBLICATIONS

Search Report dated Sep. 9, 2022 of the corresponding European patent application No. 22165095.5.
Office Action dated Jun. 6, 2022 of the corresponding Taiwan patent application No. 111104751.

* cited by examiner

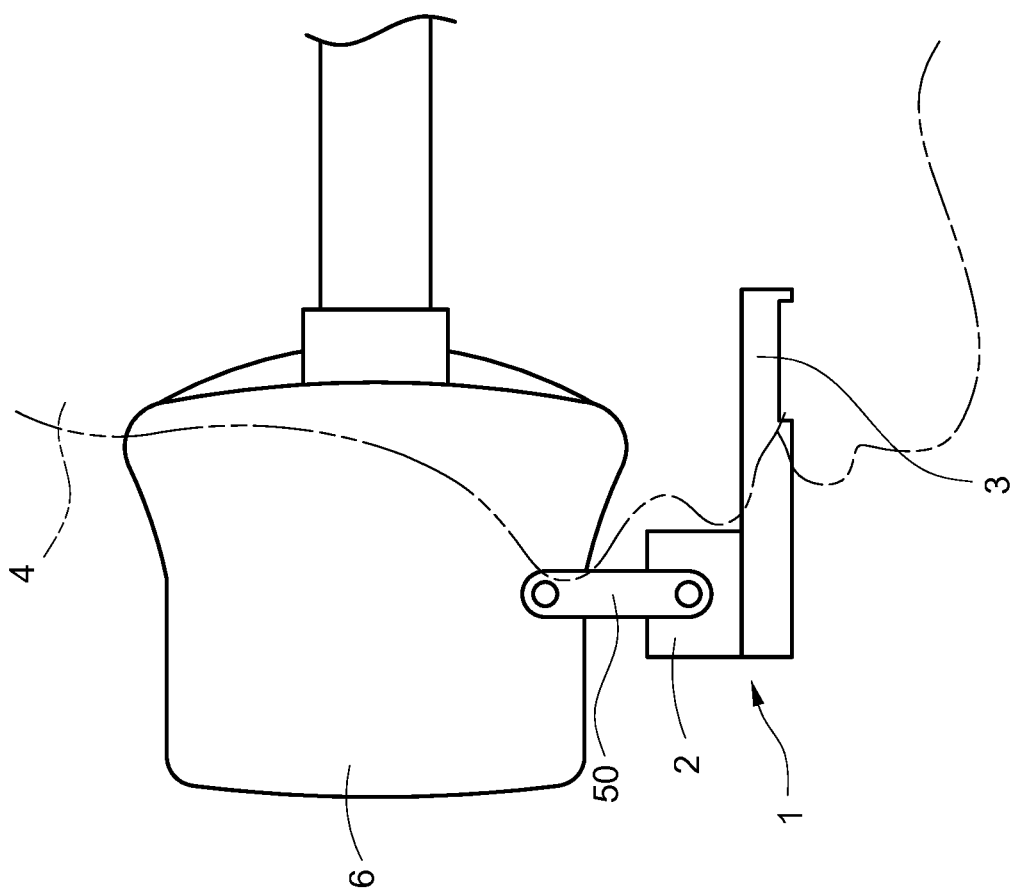

FEEDBACK DEVICE FOR SENSE OF TASTE, AND FEEDBACK SYSTEM AND FEEDBACK METHOD FOR USING THE SAME

BACKGROUND OF THE INVENTION

Technical Field

The technical field relates to a feedback device, a feedback system, and a feedback method, and specifically relates to a feedback device, a feedback system, and a feedback method for taste sense.

Description of Related Art

Recently, people become interested in immersive experiences due to the development of technologies and the change of lifestyles. The immersive experience means using technologies to build and provide essential environments and information, so that a near reality scenario may be created. Therefore, users may immerse and enjoy in the created scenario.

The most common immersive experiences, such as 4D/5D movies, immersive music, and immersive lightings, etc., may only provide sensory feedback through visual sense (such as lights, VR, AR, or projection technology, etc.), auditory sense (such as music or sound effect), tactile sense (such as water spraying, heating, or vibrating, etc.), and olfactory sense (such as spreading specific odor into the environment). However, the current immersive experiences do not provide taste feedback as one of its sensory feedback.

Taking the 4D/5D movies as an example. When the movie is played to a scene that shows a leading actor eating a specific food, the moviegoer is unable to experience the feeling of eating the specific food without having a device that can provide taste feedback for the movie.

SUMMARY OF THE INVENTION

The disclosure is directed to a feedback device, a feedback system, and a feedback method for taste sense, which may provide demanded taste feedback synchronously following the playback of the multimedia file.

In one of the exemplary embodiments, the feedback device includes:
a processor;
a container connected with the processor, storing multiple taste materials; and
a providing mechanism connected with the processor and the container;
wherein, the processor is configured to receive a control signal sent from a media player during the media player plays a multimedia file, and to control the providing mechanism to externally provide one of the multiple taste materials stored in the container in accordance with the control signal.

In one of the exemplary embodiments, the feedback system includes:
a media player, used to play a multimedia file, wherein the multimedia file comprises multiple labeled paragraphs, and the media player is configured to send a control signal when the multimedia file is played to each of the labeled paragraphs; and
a feedback device, connected with the media player to receive the control signal, comprising:
a container, stored multiple taste materials, wherein flavors provided by the multiple taste materials are respectively corresponding to the content of the multiple labeled paragraphs, and a stacking order of the multiple taste materials in the container is corresponding to a playing order of the multiple labeled paragraphs;
a providing mechanism connected with the container; and
a processor connected to the container and the providing mechanism, controlling the providing mechanism to externally provide a first one of the taste materials in the container in accordance with the control signal.

In one of the exemplary embodiments, the feedback method is applied to the feedback device and the feedback system and includes the following steps:
a) playing a multimedia file by the media player, wherein the multimedia file comprises multiple labeled paragraphs;
b) sending a control signal to the feedback device by the media player when one of the multiple labeled paragraphs is played;
c) providing a taste material by the feedback device in accordance with the control signal, wherein the feedback device stacks multiple taste materials, flavors provided by the multiple taste materials are corresponding to the content of the multiple labeled paragraphs, and a stacking order of the multiple taste materials is corresponding to a playing order of the multiple labeled paragraphs; and
d) re-executing the step a) through the step c) until the multimedia file is finished playing.

The present disclosure connects the feedback device for taste sense and the media player for multimedia file, so that the taste material provided by the feedback device may be synchronized with the content of the played multimedia file. When the multimedia file is played to a labeled paragraph, the feedback device may provide a corresponding flavor to the user's mouth. Therefore, the user may profoundly understand the deeper meaning of the content of the multimedia file through taste experience.

DESCRIPTION OF THE DRAWINGS

FIG. 9 is a schematic diagram showing a feedback system for taste sense of a first embodiment according to the present disclosure.

DETAILED DESCRIPTION OF THE INVENTION

In cooperation with the attached drawings, the technical contents and detailed description of the present invention are described hereinafter according to multiple embodiments, being not used to limit its executing scope. Any equivalent variation and modification made according to appended claims is all covered by the claims claimed by the present invention.

Figure 1:
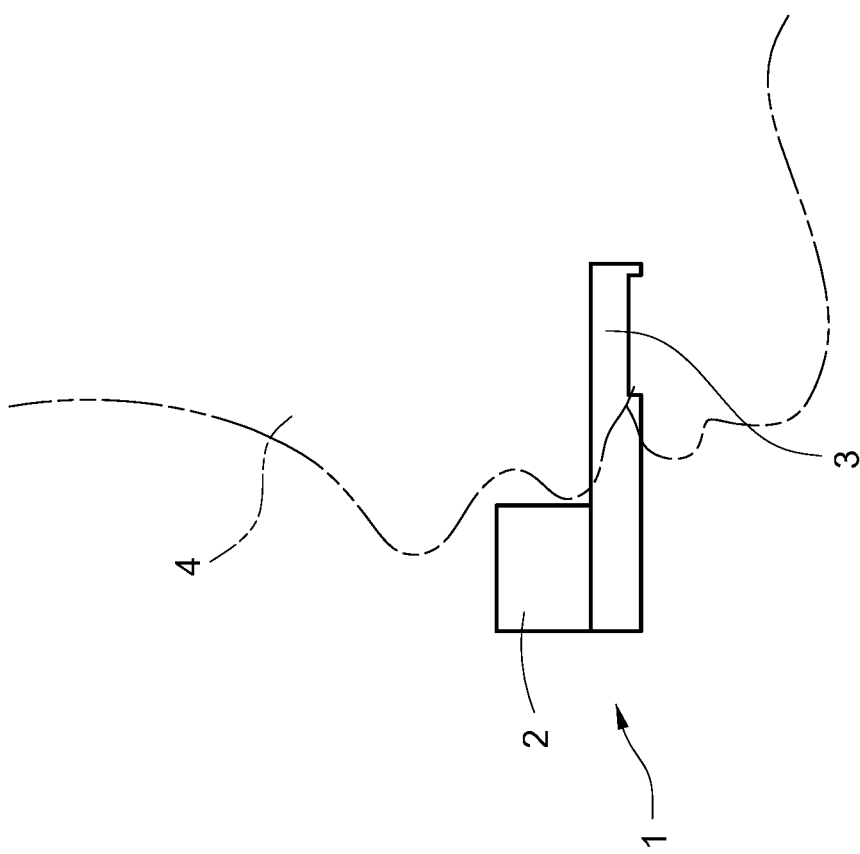
FIG. 1 is a schematic diagram of using a feedback device for taste sense of an embodiment according to the present disclosure.

Please refer to FIG. 1, which is a schematic diagram of using a feedback device for taste sense of an embodiment according to the present disclosure. As disclosed in FIG. 1, the present disclosure discloses a feedback device for taste sense (referred to as the feedback device 1 hereinafter). A user 4 may entirely or partially put the feedback device 1 in the mouth to obtain taste feedback from the feedback device 1 through taste sense.

In particular, when receiving an operation (such as receiving an internal control signal or an external control signal), the feedback device 1 may release a corresponding flavor. If the user 4 entirely or partially puts the feedback device 1 in the mouth, the flavor from the feedback device 1 may be released directly to the user's 4 mouth. Therefore, the main purpose of providing taste feedback may be achieved.

In the embodiment of FIG. 1, the feedback device 1 may be defined to include a processing part 2 and a providing part 3 on the basis of its shell, wherein the providing part 3 is extended from one side of the processing part 2, and the volume of the providing part 3 may be smaller than the volume of the processing part 2. In the embodiment, the processing part 2 is used to contain each component inside the feedback device 1 (detailed described in the following), and the providing part 3 is put in user's 4 mouth to directly provide taste feedback. However, the above description is only one embodiment of the present disclosure, but the shape and structure of the feedback device 1 of the present disclosure is not limited to the disclosure in FIG. 1.

Figure 2:
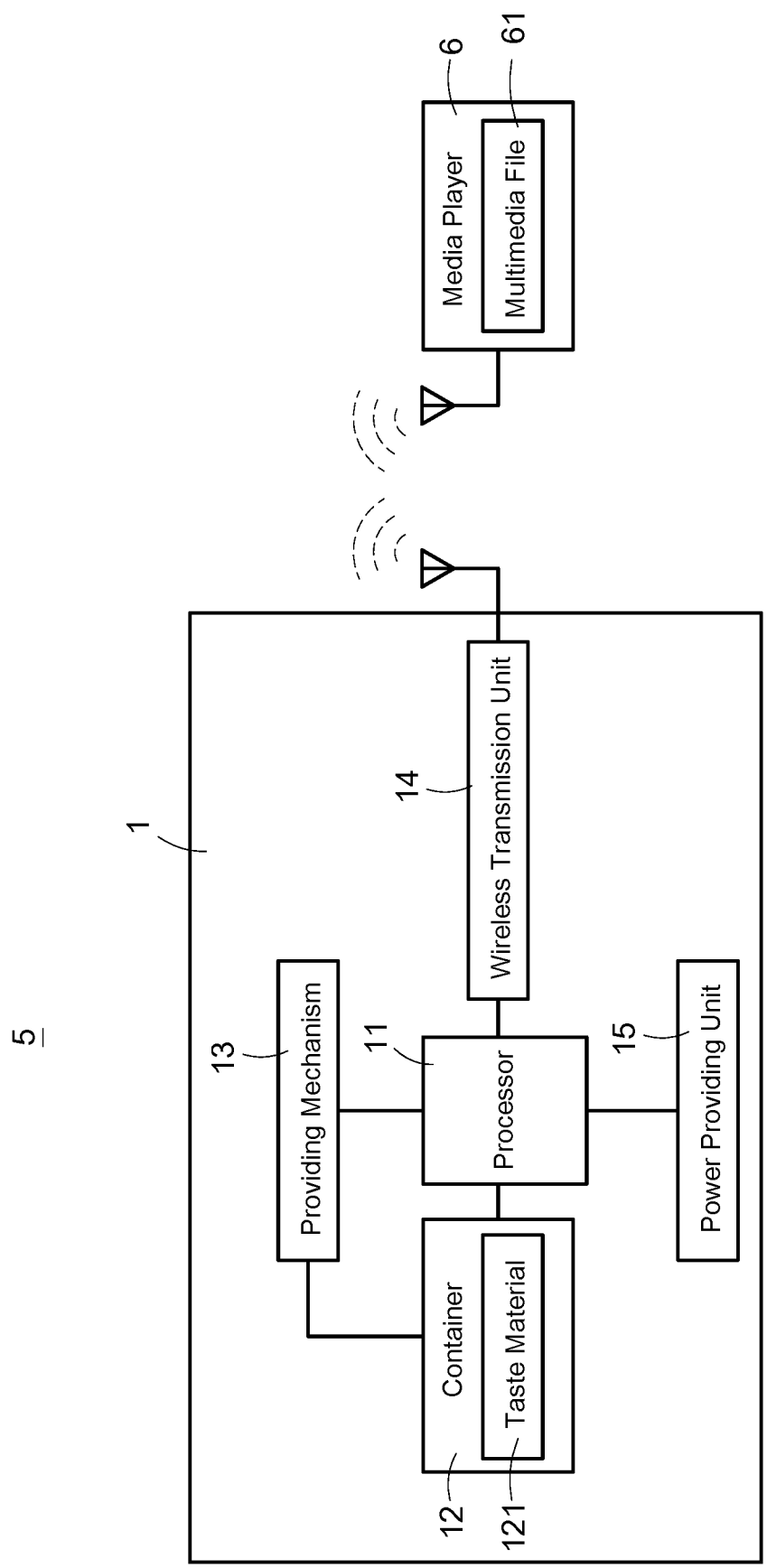
FIG. 2 is a block diagram of a feedback device for taste sense of an embodiment according to the present disclosure.
Figure 3:
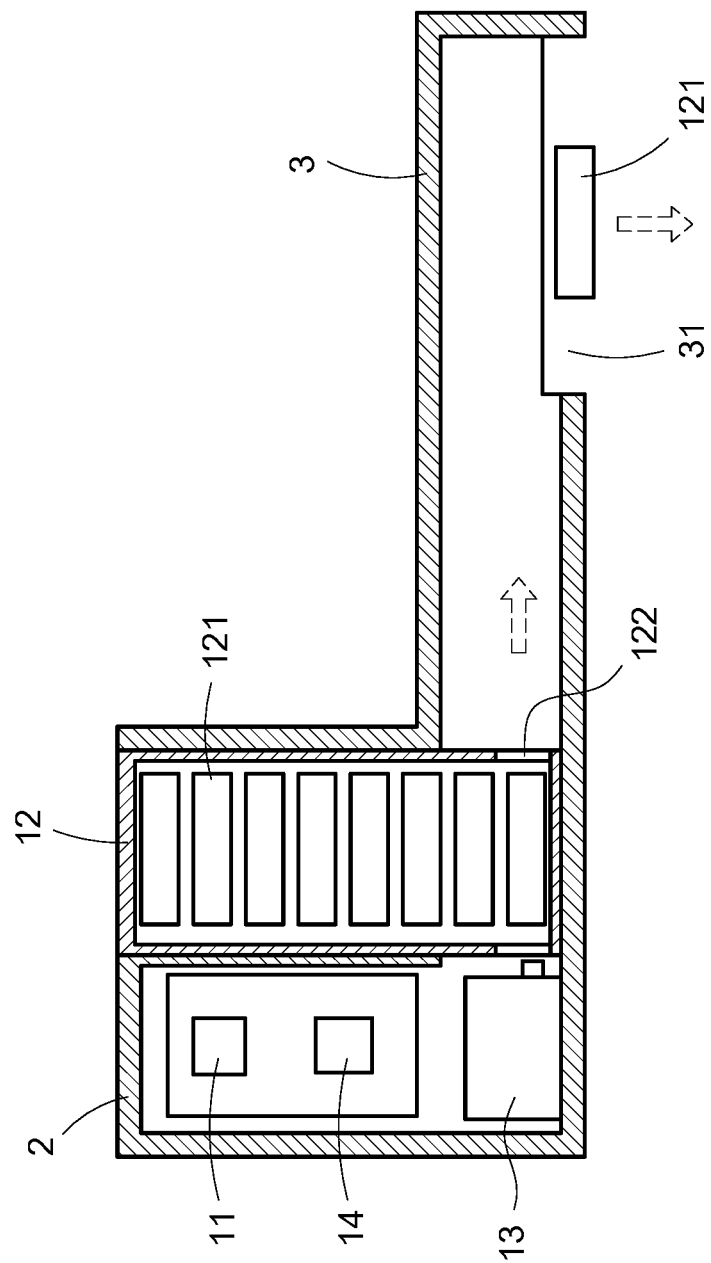
FIG. 3 is a schematic diagram of a feedback device for taste sense of an embodiment according to the present disclosure.

Please refer to FIG. 2 and FIG. 3, wherein FIG. 2 is a block diagram of a feedback device for taste sense of an embodiment according to the present disclosure, and FIG. 3 is a schematic diagram of a feedback device for taste sense of an embodiment according to the present disclosure.

The present disclosure further discloses a feedback system for taste sense (referred to as the feedback system 5 herein after), the feedback system 5 includes the aforementioned feedback device 1, and a media player 6 wirelessly connected with the feedback device 1. The media player 6 is used to play at least one multimedia file 61. The multimedia file 61 records continuously changing multimedia information, and part of the paragraphs in the multimedia information are labelled as label paragraphs. One technical feature of the present disclosure is that, when the multimedia file 61 is played by the media player 6 to any of the labeled paragraphs, the feedback device 1 may synchronously provide corresponding taste feedback. Therefore, the user 4 may taste the flavor that the labeled paragraph intended to present in the mouth through taste sense, so as to profoundly experience the deeper meaning of the multimedia file 61.

As shown in FIG. 2, the feedback device 1 of the present disclosure may include a processor 11, a container 12, a providing mechanism 13, a wireless transmission unit 14, and a power providing unit 15, wherein the container 12, the providing mechanism 13, the wireless transmission unit 14, and the power providing unit 15 are connected with the processor 11. In one embodiment, the processor 11, the container 12, the providing mechanism 13, the wireless transmission unit 14, and the power providing unit 15 are arranged inside the feedback device 1, but not limited.

The processor 11 may be, for example but not limited to, a central process unit (CPU), a micro control unit (MCU), a system on chip (SoC), a field programmable gate array (FPGA), or an application specific integrated circuit (ASIC), etc.

The power providing unit 15 may be, for example but not limited to, a disposable battery, a chargeable battery, or a power connection port used to connect to an external power source, etc. The power providing unit 15 provides power to the processor 11, so that the feedback device 1 may obtain necessary power for operation.

The wireless transmission unit 14 may be, for example but not limited to, a Wi-Fi transmission unit, a Bluetooth transmission unit, a near field communication (NFC) transmission unit, a Zigbee transmission unit, or an infrared transmission unit, etc. In the present disclosure, the feedback device 1 may wirelessly connect with the media player 6 through the wireless transmission unit 14 and reach a synchronization with the media player 6 through signal transmissions.

In another embodiment, the feedback device 1 may connect with the media player 6 through a wired manner (for example, through a connection port or a cable, etc.), it is not limited to the disclosure of FIG. 2. In particular, the feedback device 1 should be able to receive the signal sent from the media player 6 regardless the connection approach between the feedback device 1 and the media player 6. In other words, the feedback device 1 may be connected with the media player 6 through a wired manner or a wireless manner (detailed described in the following).

For brevity purpose, only a wireless manner that the feedback device 1 and the media player 6 are wirelessly connected with each other through the wireless transmission unit 14 is taken as an example in the following, but not limited thereto.

The container 12 stores multiple taste materials 121. In particular, the taste materials 121 may be edible materials made of different forms (such as solid materials or liquid materials, etc.), and the multiple taste materials 121 may be used to provide same or different flavors. The feedback device 1 of the present disclosure may release one of the taste materials 121 having a specific flavor to the user's 4 mouth, so as to achieve the technical effect of taste feedback.

In one embodiment, the container 12 may be disassembled from the feedback device 1 for replacement. Therefore, the user 4 may change the content of the taste materials 121 inside the feedback device 1, or the user 4 may change the material type of the taste materials 121 (detailed described in the following).

In particular, the media player 6 plays a multimedia file 61, wherein a plurality of labeled paragraphs (not shown) is included in the multimedia file 61. In one embodiment, the label paragraphs are paragraphs in the multimedia file 61 that have contents related with foods. In another embodiment, the label paragraphs are paragraphs in the multimedia file 61 that need delivering the atmospheres through taste sense. When the media player 6 plays the multimedia file 61 to one of the label paragraphs, the feedback device 1 may provide a flavor corresponding to this labeled paragraph to the user 4, so as to achieve the purpose of taste feedback (detailed described in the following).

The providing mechanism 13 is connected with the container 12. As disclosed in FIG. 3, the providing mechanism 13 may be arranged at one side of the container 12, and the providing mechanism 13 is used to obtain one of the taste materials 121 corresponding to the labeled paragraph from the container 12 to externally provide the obtained taste material 121.

One technical feature of the present disclosure is that the feedback device 1 and the media player 6 may be synchronized through signal transmission. The media player 6 may continuously play the multimedia file 61 after being triggered (such as a PLAY button is pressed). The multimedia file 61 records continuously changing multimedia information. In other words, the multimedia file 61 may be, for example but not limited to, a file of movie, video, music, or lighting show, etc. When the media player 6 plays the multimedia file 61 to any of the labeled paragraphs, a control signal may be generated correspondingly and transmitted to the feedback device 1 in real-time.

The feedback device 1 receives the control signal sent from the media player 6 through the wireless transmission unit 14, and the feedback device 1 transfers the control signal to the processor 11 through an internal transmission channel (not shown). The processor 11 controls the providing mechanism 13 in accordance with the control signal, so that the providing mechanism 13 obtains one of the taste materials 121 from the container 12 that is corresponding to the control signal and provide the obtained taste material 121 to the user 4.

In the embodiment of FIG. 3, the user 4 may put the providing part 3 of the feedback device 1 in the mouth, wherein the providing part 3 is arranged with an opening 31 at one side. In the embodiment, the providing mechanism 13 transfers the obtained taste material 121 to the opening 31, so that the taste material 121 may drop to the user's 4 mouth through the opening 31. The user 4 may taste a flavor that is relevant to the currently played labeled paragraph through the taste material 121 dropped from the feedback device 1, so as to achieve the technical effect of taste feedback.

In the disclosure, the multiple taste materials 121 may be stacked inside the container 12. In addition, the user 4 may arrange the content, the quantity, and the stacking order of the multiple taste materials 121 stored in the container 12 in accordance with the content of the multimedia file 61 that the user 4 wants to play. In particular, the flavors provided by the multiple taste materials 121 may be respectively corresponding to the contents that the multiple labeled paragraphs in the multimedia file 61 want to present.

In one embodiment, the quantity of the multiple taste materials 121 is same as the quantity of the multiple labeled paragraphs of the multimedia file 61, and the stacking order of the multiple taste materials 121 stacked in the container 12 is corresponding to the playing order of the multiple labeled paragraphs being played from the multimedia file 61. In the embodiment, one labeled paragraph of the multimedia file 61 may be corresponding to a single taste material 121 stored in the container 12. The user 4 may understand the deep meaning that the labeled paragraph wants to present through the taste material 121 correspondingly provided by the feedback device 1.

In another embodiment, the quantity of the multiple taste materials 121 is greater than the quantity of the multiple labeled paragraphs of the multimedia file 61. In the embodiment, one or more labeled paragraphs of the multimedia file 61 may be corresponding to multiple taste materials 121 in the container 12.

In particular, if the editor of the multimedia file 61 wants one of the labeled paragraphs to strengthen the user's 4 feeling, this labeled paragraph may be pre-arranged to corresponding to multiple taste materials 121 in the container 12. When the media player 6 plays the multimedia file 61 to this labeled paragraph, the feedback device 1 may provide multiple taste materials 121 (may have same or different flavors) that are corresponding to the played labeled paragraph simultaneously to the user 4. Therefore, the taste feeling that this labeled paragraph wants to present to the user 4 may be strengthened.

As shown in FIG. 3, the container 12 is arranged with an output opening 122 at one side, wherein the arranged position of the output opening 122 is next to the providing part 3. The providing mechanism 13 is arranged near one side of the container 12, and the arranged position of the providing mechanism 13 is corresponding to the stacked position of a first one of the taste materials 121 stacked in the container 12 (i.e., the taste material 121 in the container 12 that is most close to the output opening 122).

When the media player 6 plays the multimedia file 61 to one of the multiple labeled paragraphs, a control signal is generated and sent to the feedback device 1. When the processor 11 receives the control signal through the wireless transmission unit 14, the processor 11 controls the providing mechanism 13 to operate with the taste material 121 stored in the container 12 that is most close to the output opening 122. Therefore, the taste material 121 most closing to the output opening 122 may be forced by the providing mechanism 13 to leave the container 12 and enter the providing part 3. Next, the taste material 121 in the providing part 3 may drop to the user's 4 mouth through the opening 31 of the providing part 3.

In a first embodiment, the media player 6 may be a video playback device, and the multimedia file 61 may be a wine tasting video, wherein the multiple labeled paragraphs of the multimedia file 61 may be respectively corresponding to introduction paragraphs of different wines (for example, wines made of different years or different wineries, etc.). In the embodiment, the multiple taste materials 121 in the container 12 may respectively provide the flavor of one of the multiple wines introduced in the wine tasting video. In addition, the stacking order of the multiple taste materials 121 stacked in the container 12 may be corresponding to a playing order of the multiple introduction paragraphs for different wines in the wine tasting video.

For example, the wine tasting video may include a first labeled paragraph introducing a first wine, a second labeled paragraph introducing a second wine, and a third labeled paragraph introducing a third wine. The multiple taste materials 121 may include a first taste material used to provide the flavor of the first wine, a second taste material used to provide the flavor of the second wine, and a third taste material used to provide the flavor of the third wine.

When the media player 6 plays the wine tasting video to the first labeled paragraph, a control signal is sent to the feedback device 1 correspondingly. After receiving control signal, the processor 11 of the feedback device 1 controls the providing mechanism 13 to transfer the first taste material in the container 12 that has the flavor of the first wine to the providing part 3. When the media player 6 plays the wine tasting video to the second labeled paragraph, another control signal is sent to the feedback device 1 correspondingly. After receiving control signal, the processor 11 of the feedback device 1 controls the providing mechanism 13 to transfer the second taste material in the container 12 that has the flavor of the second wine to the providing part 3, and so on.

In a second embodiment, the media player 6 may be a light machine, and the multimedia file 61 may be a file recording a lighting show, wherein the multiple labeled paragraphs of the multimedia file 61 may be respectively corresponding to lighting combinations having different atmospheres. In the embodiment, the multiple taste materials 121 in the container 12 may respectively have the flavor that each of the atmospheres wants to present. In addition, the stacking order of the multiple taste materials 121 stacked in the container 12 may be corresponding to the presenting order of the multiple lighting combinations (i.e., multiple atmospheres).

For example, the lighting show may include a first labeled paragraph presenting a first lighting combination having a first atmosphere, a second labeled paragraph presenting a second lighting combination having a second atmosphere, and a third labeled paragraph presenting a third lighting combination having a third atmosphere. The multiple taste materials 121 may include a first taste material used to provide a first flavor needed for the first atmosphere (such as a mint flavor), a second taste material used to provide a second flavor needed for the second atmosphere (such as a vanilla flavor), and a third taste material used to provide a third flavor needed for the third atmosphere (such as a lemon flavor).

When the media player 6 plays the lighting show to the first lighting combination (i.e., the first labeled paragraph), a control signal is sent to the feedback device 1 correspondingly. After receiving control signal, the processor 11 of the feedback device 1 controls the providing mechanism 13 to transfer the first taste material in the container 12 that has the flavor corresponding to the first atmosphere to the providing part 3. When the media player 6 plays the lighting show to the second lighting combination (i.e., the second labeled paragraph), another control signal is sent to the feedback device 1 correspondingly. After receiving control signal, the processor 11 of the feedback device 1 controls the providing mechanism 13 to transfer the second taste material in the container 12 that has the flavor corresponding to the second atmosphere to the providing part 3, and so on.

In a third embodiment, the media player 6 may be a movie projecting machine, and the multimedia file 61 may be a movie, wherein the multiple labeled paragraphs of the multimedia file 61 may be respectively corresponding to scenes appearing different foods. In the embodiment, the multiple taste materials 121 in the container 12 may respectively have the flavor of one of the foods that is appeared in the movie. In addition, the stacking order of the multiple taste materials 121 stacked in the container 12 may be corresponding to the appearing order of the multiple foods in the movie.

For example, the movie may include a first labeled paragraph showing a male protagonist eating a first food and a second labeled paragraph showing a heroine eating a second food. The multiple taste materials 121 may include a first taste material used to provide the flavor of the first food and a second taste material used to provide the flavor of the second food.

When the media player 6 plays the movie to the first labeled paragraph, a control signal is sent to the feedback device 1 correspondingly. After receiving control signal, the processor 11 of the feedback device 1 controls the providing mechanism 13 to transfer the first taste material in the container 12 that has the flavor of the first food to the providing part 3. When the media player 6 plays the movie to the second labeled paragraph, another control signal is sent to the feedback device 1 correspondingly. After receiving control signal, the processor 11 of the feedback device 1 controls the providing mechanism 13 to transfer the second taste material in the container 12 that has the flavor of the second food to the providing part 3.

In a fourth embodiment, the media player 6 may be an audio device, and the multimedia file 61 may be a music, wherein the multiple labeled paragraphs of the multimedia file 61 may be respectively corresponding to music segments having different atmospheres. In the embodiment, the multiple taste materials 121 in the container 12 may respectively have the flavor that each of the atmospheres wants to present. In addition, the stacking order of the multiple taste materials 121 stacked in the container 12 may be corresponding to the playing order of the multiple music segments in the music.

For example, the music may include a first labeled paragraph corresponding to a first music segment having a first atmosphere, a second labeled paragraph corresponding to a second music segment having a second atmosphere, and a third labeled paragraph corresponding to a third music segment having a third atmosphere. The multiple taste materials 121 may include a first taste material used to provide a flavor needed for the first atmosphere, a second taste material used to provide a flavor needed for the second atmosphere, and a third taste material used to provide a flavor needed for the third atmosphere.

When the media player 6 plays the music to the first music segment (i.e., the first labeled paragraph), a control signal is sent to the feedback device 1 correspondingly. After receiving control signal, the processor 11 of the feedback device 1 controls the providing mechanism 13 to transfer the first taste material in the container 12 that has the flavor corresponding to the first atmosphere to the providing part 3. When the media player 6 plays the music to the second music segment (i.e., the second labeled paragraph), another control signal is sent to the feedback device 1 correspondingly. After receiving control signal, the processor 11 of the feedback device 1 controls the providing mechanism 13 to transfer the second taste material in the container 12 that has the flavor corresponding to the second atmosphere to the providing part 3, and so on.

It should be mentioned that the media player 6 of the present disclosure may be a combination of the aforementioned devices (such as a combination of the light machine and the audio device), and the multimedia file 61 may be a combination of the aforementioned multimedia information. In other words, the feedback device 1 of the present disclosure may provide multiple types of taste feedback correspondingly and simultaneously in accordance with multiple played contents, and not only limited to the above disclosure.

However, the above descriptions are only few embodiments of the present disclosure, but not intended to limit the scope of the present disclosure.

In a fifth embodiment, the media player 6 may be a virtual reality (VR) device and is connected with the feedback device 1 through a wireless manner or a wired manner.

Please refer to FIG. 9, which is a schematic diagram showing a feedback system for taste sense of a first embodiment according to the present disclosure. As disclosed in FIG. 9, the media player 6 may be a VR device, and the feedback device 1 may be an extension device extended from the VR device. In the embodiment, the media player 6 is connected with the feedback device 1 through a connection structure 50. When the user 4 puts the media player 6 on the head, the feedback device 1 may be located near the user's 4 mouth, so that the user 4 may easily put the providing part 3 of the feedback device 1 in the mouth.

In one embodiment, the connection structure 50 is a pure mechanical structure (such as a connecting port) and is used to pivoted connect the media player 6 with the feedback device 1. Therefore, the feedback device 1 may move relative to the media player 6. In the embodiment, the feedback device 1 wirelessly connects the media player 6 through the wireless transmission unit 14 to receive the control signal sent from the media player 6.

In another embodiment, the connection structure 50 is a combination of a mechanical structure and an electronic structure (for example, a connection port and a connection cable are included in the connection structure 50) and is used to electrically connect the media player 6 with the feedback device 1. In the embodiment, the feedback device 1 connects the media player 6 to receive the control signal sent from the media player 6 through a wired manner or a wireless manner.

Moreover, the media player 6 and the feedback device 1 may be same device (for example, the media player 6 and the feedback device 1 may be integrated inside a single VR device), and the media player 6 and the feedback device 1 may share same processor 11 (such as the processor 11 shown in FIG. 2). In other words, the processor 11 may be arranged inside the shell of the feedback device 1 (such as inside the processing part 2) or arranged inside the shell of the media player 6. In another embodiment, the media player 6 and the feedback device 1 may be two individual devices, and each of the media player 6 and the feedback device 1 has an independent processor.

Figure 4:
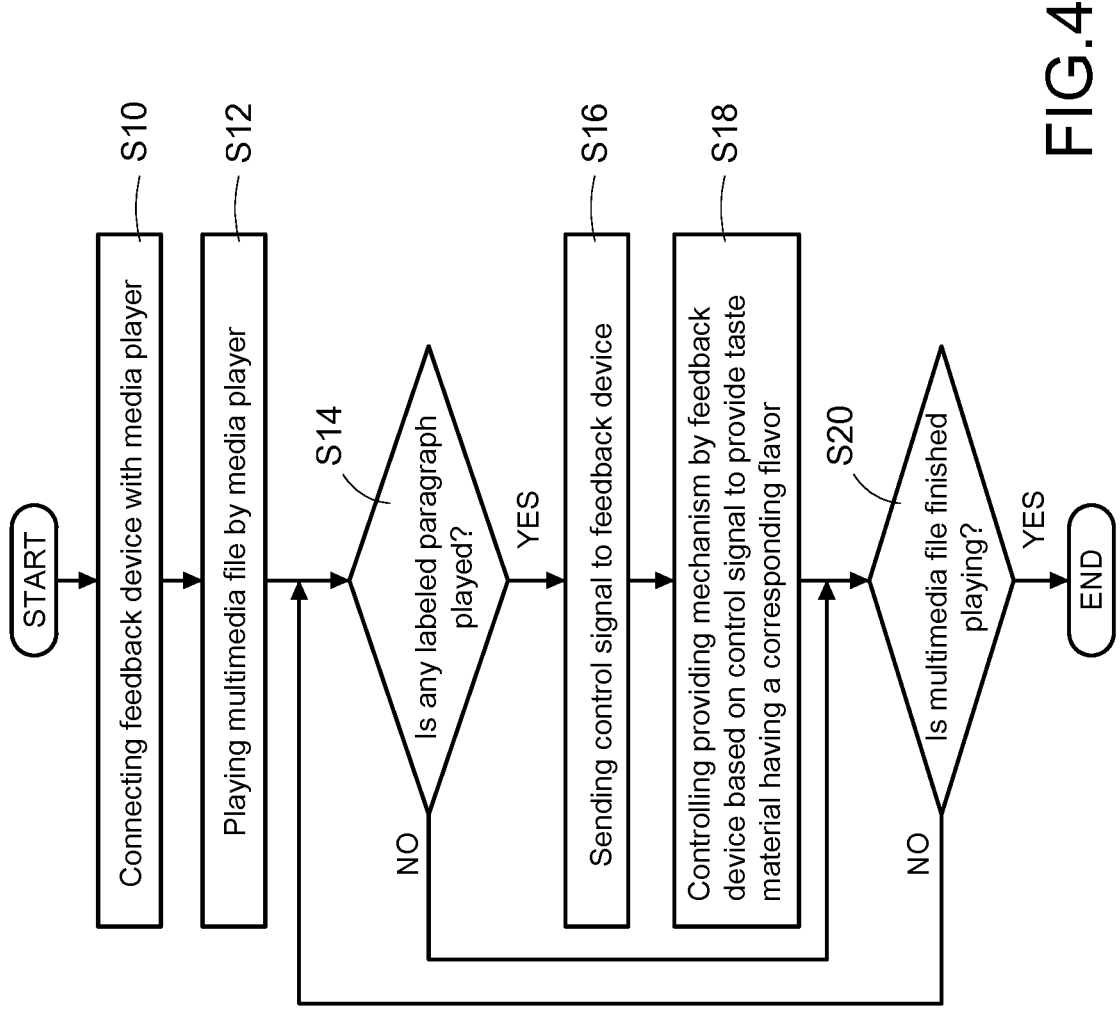
FIG. 4 is a flowchart of a feedback method for taste sense of an embodiment according to the present disclosure.

Please refer to FIG. 4, which is a flowchart of a feedback method for taste sense of an embodiment according to the present disclosure. The present disclosure further discloses a feedback method for taste sense (referred to as the feedback method hereinafter), the feedback method is applied to the feedback device 1 and the feedback system 5 as disclosed in FIG. 1, FIG. 2, and FIG. 3, but not limited thereto.

To perform the feedback method of the present disclosure, the user 4 needs to first connect the feedback device 1 with the media player 6 (step S10). After the feedback device 1 and the media player 6 are connected, the media player 6 is operated to play the multimedia file 61 (step S12).

As disclosed above, one purpose of the present disclosure is for the feedback device 1 to provide a corresponding flavor to the user 4 in real-time once the multimedia file 61 is played to a specific paragraph (such as one of multiple labeled paragraphs). In order to achieve the purpose, the status of the taste materials 121 stored in the feedback device 1 should be consistent with the status of the labeled paragraphs included in the multimedia file 61.

When playing the multimedia file 61, the media player 6 continuously determines whether any of the labeled paragraphs is played (step S14). As discussed above, the multimedia file 61 records continuously changing multimedia information, so that the media player 6 continuously plays the multimedia file 61 before a labeled paragraph is reached, until the multimedia file 61 is finished playing.

If the media player 6 determines in the step S14 that any of the labeled paragraphs is played, the media player 6 generates a control signal correspondingly and sends the control signal to the feedback device 1 (step S16). In a first embodiment, the control signal may indicate that one of the multiple labeled paragraphs of the multimedia file 6 is played. In a second embodiment, the control signal may indicate the specific labeled paragraph of the multimedia file 6 being played. In a third embodiment, the control signal carries the information related to the flavor corresponding to this labeled paragraph. However, the above description are only few embodiments of the present disclosure, but not limited thereto.

After the step S16, the feedback device 1 receives the control signal sent from the media player 6 through the wireless transmission unit 14. In addition, the processor 11 of the feedback device 1 controls the providing mechanism 13 and/or the container 12 in accordance with the control signal to provide one of the taste materials 121 that has the flavor corresponding to the specific labeled paragraph to the user 4 (step S18).

In one embodiment, the processor 11 controls the providing mechanism 13 based on the control signal, so that the providing mechanism 13 transfers a first one of the multiple taste materials 121 in the container 12 (for example, the taste material 121 that is most close to the output opening 122 of the container 12) to the providing part 3 of the feedback device 1. After entering the providing part 3, the taste material 121 may drop into the user's 4 mouth through the opening 31 on the providing part 3. The user 4 may taste the flavor that the specific labeled paragraph wants to present through eating the taste material 121 provided by the feedback device 1. Therefore, the technical effect of taste feedback may be achieved.

After the step S18, the media player 6 and/or the feedback device 1 determines whether the multimedia file 61 is finished playing (step S20). If the multimedia file 61 is yet finished playing, the media player 6 and/or the feedback device 1 goes back to the step S14 and re-executes the step S14 through the step S18 to continuously play the multimedia file 61 and to continuously determine whether any of the labeled paragraphs is played. When the multimedia file 61 is finished playing, the feedback method of the present disclosure may be terminated.

As discussed above, the status of the taste materials 121 stored in the feedback device 1 should be corresponding to the status of the labeled paragraphs included in the multimedia file 61. For example, the quantity of the multiple taste materials 121 is same as the quantity of the multiple labeled paragraphs, and the flavors provided by the taste materials 121 are respectively corresponding to the flavors that the labeled paragraphs want to present. In one embodiment, after the multimedia file 61 is finished playing, the taste materials 121 in the feedback device 1 are finished releasing as well.

In the present disclosure, the feedback device 1 processes the received control signal by the processor 11, so as to control the providing mechanism 13 to provide a corresponding one of the taste materials 121 in the container 12 to the user 4. Hence, the type of the providing mechanism 13 arranged in the feedback device 1 should corresponding to the type of the taste materials 121 stored in the container 12 (detailed described in the following).

Figure 5:
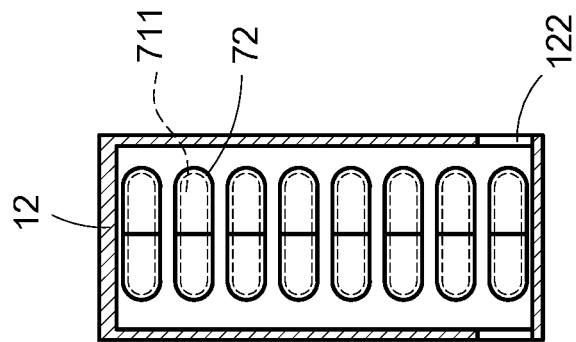
FIG. 5 is a schematic diagram showing a taste material of a first embodiment according to the present disclosure.

Please refer to FIG. 5, which is a schematic diagram showing a taste material of a first embodiment according to the present disclosure. In the embodiment, multiple taste materials 71 are solid materials stacked in the container 12. The solid material may be, for example, an edible paper (such as a rice paper membrane), and the edible paper absorbs liquid material 711 that has a corresponding flavor.

In particular, the manufacturer of the feedback device 1 may pre-analyze a target flavor to extract the composition of the target flavor, and then the manufacturer may produce the liquid material 711 having the target flavor through compound or composition. After attaching the liquid material 711 to the edible paper that does not have a special flavor, the edible paper may be transformed into the solid taste material 71 of the present embodiment.

In the embodiment, the providing mechanism 13 may be an ejection mechanism arranged at one side of the container 12 (as shown in FIG. 3), and the arrangement position of the ejection mechanism is corresponding to the stored position of a first one of the multiple taste materials 71 stored in the container 12 (i.e., the taste material 71 that is most close to the output opening 122). When receiving the control signal sent from the media player 6 due to a labeled paragraph being played, the processor 11 controls the providing mechanism 13 to eject the first one of the taste materials 71 from the container 12 to the providing part 3. Therefore, the taste material 71 in the providing part 3 may drop into the user's 4 mouth through the opening 31, so as to provide the flavor that the labeled paragraph wants to present to the user 4.

Figure 6:
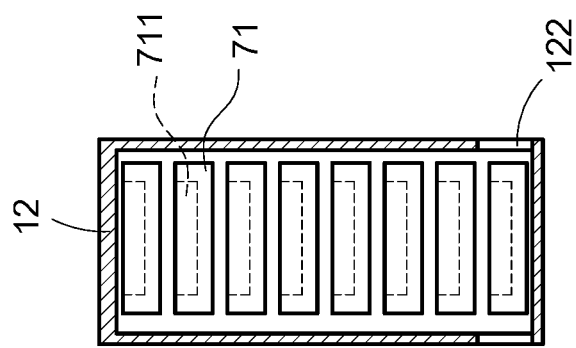
FIG. 6 is a schematic diagram showing a taste material of a second embodiment according to the present disclosure.

Please refer to FIG. 6 at the same time, wherein FIG. 6 is a schematic diagram showing a taste material of a second embodiment according to the present disclosure.

In the embodiment, multiple taste materials 72 are solid materials (such as capsules) stacked in the container 12, and each of the capsules contains liquid material 711 that has a corresponding flavor.

In the embodiment, the providing mechanism 13 may be an ejection mechanism arranged at one side of the container 12 (as shown in FIG. 3), and the arrangement position of the ejection mechanism is corresponding to the stored position of a first one of multiple taste materials 72 stored in the container 12 (i.e., the taste material 72 that is most close to the output opening 122).

When receiving the control signal sent from the media player 6 due to a labeled paragraph being played, the processor 11 controls the providing mechanism 13 to eject the first one of the taste materials 72 from the container 12 to the providing part 3. Therefore, the taste material 72 in the providing part 3 may drop into the user's 4 mouth through the opening 31. In the embodiment, the shell of the capsule may be dissolved by saliva in user's 4 mouth, and the liquid material 711 in the capsule may be released into the user's 4 mouth after the shell of the capsule is dissolved. Therefore, the flavor that the labeled paragraph wants to present may be provided to the user 4 through the liquid material 711 being released.

Figure 7:
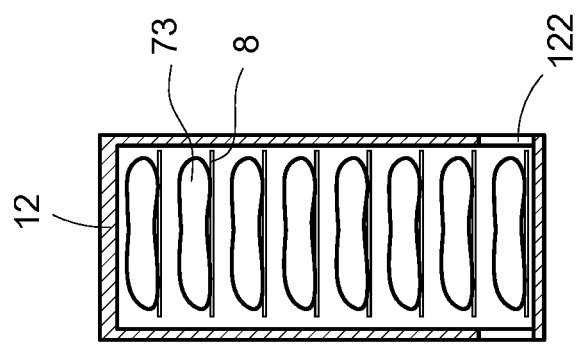
FIG. 7 is a schematic diagram showing a taste material of a third embodiment according to the present disclosure.

Please refer to FIG. 7 at the same time, wherein FIG. 7 is a schematic diagram showing a taste material of a third embodiment according to the present disclosure.

In the embodiment, multiple taste materials 73 are liquid materials or muddy materials stacked in the container 12. In particular, after analyzing a target flavor and extract the composition of the target flavor, the manufacturer of the feedback device 1 may produce the liquid material or the muddy material having the target flavor through compound or composition.

In the embodiment, the providing mechanism 13 is an extrusion mechanism arranged at one side of the container 12, and the arrangement position of the extrusion mechanism is corresponding to the stored position of a first one of the taste materials 73 stored in the container 12 (i.e., the taste material 73 that is most close to the output opening 122). When receiving the control signal sent from the media player 6 due to a labeled paragraph being played, the processor 11 controls the providing mechanism 13 to extrude the first one of the taste materials 73 from the container 12 to the providing part 3. Therefore, the taste material 73 in the providing part 3 may flow into the user's 4 mouth through the opening 31, so as to provide the flavor that the labeled paragraph wants to present to the user 4.

Unlike the solid materials, stacking multiple liquid materials or multiple muddy materials having different flavors together may cause a change in the taste. As shown in FIG. 7, the container 12 may further have at least one blocking material 8 therein. The blocking material 8 may be produced by an edible material (such as a rice paper membrane) and arranged between two taste materials 73 having different flavors. Therefore, even if the liquid materials or the muddy materials are used, the feedback device 1 may still stack the taste materials in the container 12.

Figure 8:
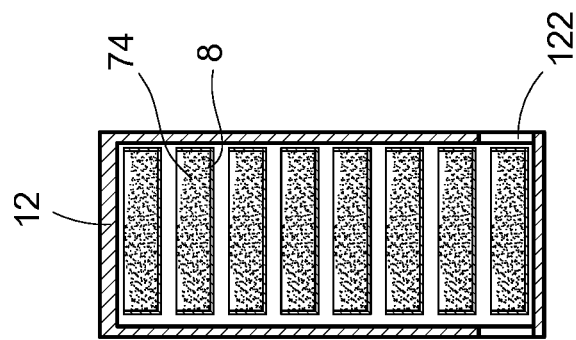
FIG. 8 is a schematic diagram showing a taste material of a fourth embodiment according to the present disclosure.

Please refer to FIG. 8 at the same time, where in FIG. 8 is a schematic diagram showing a taste material of a fourth embodiment according to the present disclosure.

In the embodiment, multiple taste materials 74 are liquid materials, gas materials, or powdery materials stacked in the container 12. In particular, after analyzing a target flavor and extract the composition of the target flavor, the manufacturer of the feedback device 1 may produce the liquid material, the gas material, or the powdery material having the target flavor through compound or composition.

In the embodiment, the providing mechanism 13 is a spraying mechanism arranged at one side of the container 12, and the arrangement position of the spraying mechanism is corresponding to the stored position of a first one of the taste materials 74 in the container 12 (i.e., the taste material 74 that is most close to the output opening 122). When receiving the control signal sent from the media player 6 due to a labeled paragraph being played, the processor 11 controls the providing mechanism 13 to spray the first one of the taste materials 74 from the container 12 to the providing part 3. Therefore, the taste material 74 in the providing part 3 may drip to the user's 4 mouth through the opening 31, so as to provide the flavor that the labeled paragraph wants to present to the user 4.

As mentioned above, stacking multiple liquid materials, multiple gas materials, or multiple powdery materials having different flavors together may cause a change in the taste. In the embodiment of FIG. 8, the container 12 uses at least one blocking material 8 to block two taste materials 74 having different flavors. Therefore, the taste materials 74 may be stacked in the container 12 no matter liquid materials, gas materials, or powdery materials are used.

To prevent the solid material, the liquid material, the gas material, the muddy material, or the powdery material stored in the container 12 from spilling over the container 12 before using, the container 12 of the present disclosure may be arranged with a baffle (not shown) at a position of the output opening 122. The baffle may block the taste materials 71-74 in the container 12 when the baffle is unstressed. When being controlled by the processor 11, the providing mechanism 13 externally exerts force. The baffle receives the force to open, so that the taste materials 71-74 may leave the container 12 through the output opening 122 and enter the providing part 3.

However, the above description is only one embodiment of the present disclosure, but not limited thereto.

It should be mentioned that the user 4 may replace the container 12 of the feedback device 1; therefore, the user 4 does not have to change the entire feedback device 1 when the user 4 wants to change the taste materials 121. As a result, unnecessary waste is prevented.

Figure 10:
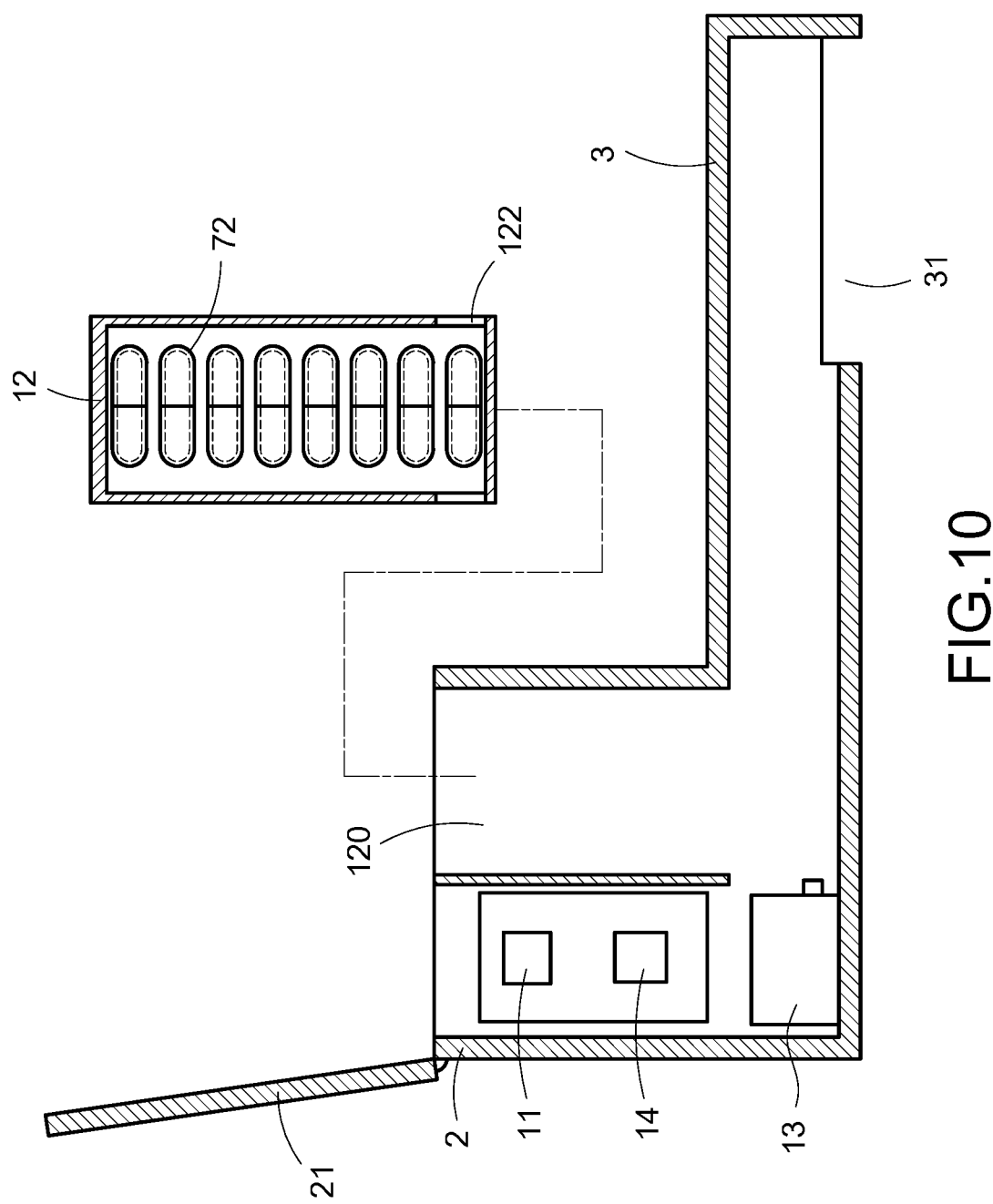
FIG. 10 is a schematic diagram showing a feedback system for taste sense of a second embodiment according to the present disclosure.

Please refer to FIG. 10, which is a schematic diagram showing a feedback system for taste sense of a second embodiment according to the present disclosure. As disclosed in FIG. 10, one side of the processing part 2 of the feedback device 1 may be arranged with a flip cover 21. When the flip cover 21 is flipped off, the container 12 may be pulled out of a replacement space 120 in the processing part 2, so that the user 4 may replace the container 12 of the feedback device 1.

In particular, when the user 4 wants to change the multimedia file 61 played by the media player 6, the user 4 should replace the container 12 of the feedback device 1 simultaneously. Therefore, the taste materials 121 provided by the feedback device 1 and the content of the multimedia file 61 played by the media player 6 may remain consistent.

In one embodiment, the user 4 may replace the container 12 of the feedback device 1 based on mood or preference, so that the user 4 may use a demanded material type. In the embodiment of FIG. 10, the user 4 replaces the container 12 (such as a container 12 storing taste materials 71 of edible paper) in the replacement space 120 with another container 12 storing taste materials 72 of capsule. According to the technical solution, a problem that some material types (such as liquid material or muddy material, etc.) are unwelcome to the user 4 may be resolved.

By using the feedback device, the feedback system, and the feedback method of the present disclosure, the user may obtain taste feedback through the taste materials while enjoy the content of the multimedia through visual sense, auditory sense, tactile sense, and olfactory sense. Therefore, the user may profoundly understand the deeper meaning that the multimedia content wants to present through taste experience.

As the skilled person will appreciate, various changes and modifications can be made to the described embodiment. It is intended to include all such variations, modifications and equivalents which fall within the scope of the present invention, as defined in the accompanying claims.

What is claimed is:

1. A feedback device for taste sense, comprising:
 a processor;
 a container connected with the processor, storing multiple taste materials;
 a providing mechanism connected with the processor and the container; and
 a processing part and a providing part extended from one side of the processing part;
 wherein, the processor is configured to receive a control signal sent from a media player during the media player plays a multimedia file, and to control the providing mechanism to externally provide one of the multiple taste materials stored in the container in accordance with the control signal;
 wherein the container and the providing mechanism are arranged in the processing part, the providing part is used for a user to put in the mouth, the providing part comprises an opening at one side, and the providing mechanism is configured to provide the taste material through the opening;
 wherein the providing mechanism is an ejection mechanism arranged at one side of the container, the multiple taste materials are solid materials stacked in the container, and the ejection mechanism is controlled by the processor to eject a first one of the taste materials stacked in the container to the providing part;
 wherein the multiple taste materials are rice paper membranes respectively absorbing a liquid material having a corresponding flavor or capsules respectively containing the liquid material having the corresponding flavor.

2. The feedback device in claim 1, wherein the container comprises at least one blocking material, the blocking material is arranged between two taste materials having different flavors.

3. The feedback device in claim 1, wherein the control signal is corresponding to one of multiple labeled paragraphs comprised in the multimedia file, the flavors provided by the multiple taste materials are respectively corresponding to the content of the multiple labeled paragraphs, and a stacking order of the multiple taste materials stacked in the container is corresponding to a playing order of the multiple labeled paragraphs.

4. A feedback system for taste sense, comprising:
 a media player, used to play a multimedia file, wherein the multimedia file comprises multiple labeled paragraphs, and the media player is configured to send a control signal when the multimedia file is played to each of the labeled paragraphs; and
 a feedback device, connected with the media player to receive the control signal, comprising:
 a container, stored multiple taste materials, wherein flavors provided by the multiple taste materials are respectively corresponding to the content of the multiple labeled paragraphs, and a stacking order of the multiple taste materials in the container is corresponding to a playing order of the multiple labeled paragraphs;
 a providing mechanism connected with the container;
 a processing part and a providing part extended from one side of the processing part; and
 a processor connected to the container and the providing mechanism, controlling the providing mechanism to externally provide a first one of the taste materials in the container in accordance with the control signal;
 wherein the container and the providing mechanism are arranged in the processing part, the providing part is used for a user to put in the mouth, the providing part comprises an opening at one side, and the providing mechanism is configured to provide the taste material through the opening;
 wherein the providing mechanism is an ejection mechanism arranged at one side of the container, the multiple taste materials are solid materials stacked in the container, and the ejection mechanism is controlled by the processor to eject the first one of the taste materials stacked in the container to the providing part;
 wherein the multiple taste materials are rice paper membranes respectively absorbing a liquid material having a corresponding flavor or capsules respectively containing the liquid material having the corresponding flavor.

5. The feedback system in claim 4, wherein the media player is a video playback device, the multimedia file is a wine tasting video, the multiple labeled paragraphs are respectively corresponding to different introduction paragraphs of different wines, and the multiple taste materials are respectively having different flavors of the wines.

6. The feedback system in claim 4, wherein the media player is a light machine, the multimedia file is a file recording a lighting show, the multiple labeled paragraphs are respectively corresponding to different lighting combinations having different atmospheres, and the multiple taste materials are respectively corresponding to different flavors needed by the atmospheres.

7. A feedback method for taste sense, applied to a feedback system comprising a feedback device and a media player, comprising:
 a) playing a multimedia file by the media player, wherein the multimedia file comprises multiple labeled paragraphs;
 b) sending a control signal to the feedback device by the media player when one of the multiple labeled paragraphs is played;

c) providing a taste material by the feedback device in accordance with the control signal, wherein the feedback device stacks multiple taste materials, flavors provided by the multiple taste materials are respectively corresponding to the content of the multiple labeled paragraphs, and a stacking order of the multiple taste materials is corresponding to a playing order of the multiple labeled paragraphs; and d) re-executing the step a) through the step c) until the multimedia file is finished playing;

wherein the feedback device comprises a processing part and a providing part extended from one side of the processing part, wherein a container and a providing mechanism of the feedback device are arranged in the processing part, the providing part is used for a user to put in the mouth, the providing part comprises an opening at one side, and the feedback device is configured to provide the taste material through the opening;

wherein the providing mechanism is an election mechanism arranged at one side of the container, the multiple taste materials are solid materials stacked in the container and the ejection mechanism is controlled to eject a first one of the taste materials stacked in the container to the providing part:

wherein the multiple taste materials are rice paper membranes respectively absorbing a liquid material having a corresponding flavor or capsules respectively containing the liquid material having the corresponding flavor.

* * * * *